United States Patent [19]

Meucci et al.

[11] Patent Number: 5,135,875
[45] Date of Patent: Aug. 4, 1992

[54] PROTEIN PRECIPITATION REAGENT

[75] Inventors: Victoria P. Meucci, Chicago; Elizabeth A. Simpson, Skokie; Mariola B. Zajac, Chicago, all of Ill.

[73] Assignee: Abbott Laboratories, Abbott Park, Ill.

[21] Appl. No.: 567,853

[22] Filed: Aug. 15, 1990

[51] Int. Cl.$^5$ .................. G01N 33/543; G01N 33/53
[52] U.S. Cl. .................... 436/518; 436/175; 436/501; 436/17; 436/800; 436/808; 436/825; 435/7.1; 435/961; 435/962; 435/975
[58] Field of Search ............... 436/518, 501, 175, 17, 436/808, 546, 825; 435/961, 962, 968, 7.1; 524/413; 424/54, 55, 642; 25.2/408.1

[56] References Cited

U.S. PATENT DOCUMENTS

| | | | |
|---|---|---|---|
| 3,949,072 | 4/1976 | Tenta et al. | 424/145 |
| 4,022,880 | 5/1977 | Vinson et al. | 424/49 |
| 4,160,821 | 7/1979 | Sipos | 424/49 |
| 4,339,432 | 7/1982 | Ritchey et al. | 424/54 |
| 4,734,378 | 3/1988 | Wang et al. | 436/175 |

OTHER PUBLICATIONS

Ratermann et al., "Chemical Coagulation of Industrial Animal Blood Using Aluminum Sulfate, Zinc Sulfate, Methand and Acetone", J. Agric. Food Chem., 28(2):438-441 (1980).

Abstract, Soviet Union Patent 1109170 from World Patent Index (Aug. 23, 1984).

Primary Examiner—Esther L. Kepplinger
Assistant Examiner—Carol E. Bidwell
Attorney, Agent, or Firm—Daniel W. Collins; Thomas M. Breininger

[57] ABSTRACT

A precipitation reagent for use in analytical systems for the determination of hydrophobic analytes in a biological test sample, particularly analytical systems employing specific binding proteins for such analytes. The precipitation reagent precipitates interfering proteins, hemoglobin, and other interfering substances from a biological test sample while, at the same, maintaining hydrophobic analytes in solution and minimizing the denaturation of specific binding proteins, such as, for example, antibodies, which may be present in an immunoassay system. The precipitation reagent comprises a zinc salt, a glycol, and a straight or branced alcohol from about 1 to 4 carbon atoms, and may optionally contain an acid. A preferred precipitation reagent comprises zinc sulfate, methanol and ethylene glycol, and is particularly useful in a fluorescent polarization immunoassay for the determination of hydrophobic analytes, especially cyclosporine.

20 Claims, 2 Drawing Sheets

Cyclosporine in Serum/Plasma
Specific Monoclonal Antibody

PROTEIN PRECIPITATION REAGENT

FIELD OF THE INVENTION

The present invention relates to reagents which are useful for precipitating proteins from a liquid test sample. In particular, the present invention relates to reagents which extract analytes, particularly hydrophobic analytes, and precipitate interfering proteins from biological test samples to permit the measurement of such analytes present therein.

BACKGROUND OF THE INVENTION

The monitoring of therapeutic drug levels and other analytes in biological fluids such as serum, plasma, whole blood, urine and the like has become very useful to provide physicians with information to aid in proper patient management. For example, adjustment of patient dosage, achievement of optimal therapeutic effects, and avoiding useless subtherapeutic or harmful toxic dosage levels can be provided. Conventional techniques which are employed to monitor drug levels or detect other analytes are known and include radioimmunoassays and nonisotopic assays such as fluorescence polarization immunoassays. However, such techniques produce inconsistencies in results because of, for example, variations in the protein concentration of individual patient test samples and the tendency of analytes to bind to such proteins, to thereby prevent the accurate determination thereof.

Although various precipitation reagents have been described to remove or extract such interfering proteins from a test sample, such reagents suffer from a number of disadvantages, particularly for the determination of hydrophobic analytes. For example, U.S. Pat. No. 4,734,378 describes the use of 5-sulfosalicylic acid for extracting digoxin and precipitating protein from a biological test sample, and the use of zinc salts as precipitation reagents have also been described. However, such precipitation reagents do not maintain hydrophobic analytes in solution and, furthermore, 5-sulfosalicylic acid does not remove hemoglobin from, for example, a whole blood test sample. Moreover, precipitation reagents which have been previously described typically denature and thereby result in significant loss of the binding activity of, for example, antibodies employed in an immunoassay system.

SUMMARY OF THE INVENTION

The present invention relates to the discovery that analytical systems for the determination of a hydrophobic analyte in a biological test sample, particularly analytical systems employing specific binding proteins for such analytes, can be substantially improved by employing the precipitation reagent of the present invention which extracts such analyte and precipitates interfering proteins. In particular, such precipitation reagent has unexpectedly and surprisingly been found to precipitate interfering proteins, such as hemoglobin, and other interfering substances from a biological test sample while, at the same, maintaining hydrophobic analytes in solution and minimizing the denaturation of specific binding proteins, such as, for example, antibodies, which may be present in an immunoassay system. The precipitation reagent of the present invention is particularly useful in a fluorescent polarization immunoassay for the determination of hydrophobic analytes such as steroids, drugs such as cyclosporine, and analogs thereof, and the like.

The precipitation reagent of the present invention comprises from between about 5.0 mM and about 100.0mM of a zinc salt, from between about 30% (w/v) and about 100% (w/v) of a straight or branched chain alcohol having from 1 to 4 carbon atoms, and from between about 5% (w/v) and about 50% (w/v) of a glycol. The precipitation reagent may further comprise from between about 0% (w/v) and about 20 (w/v) of an acid.

DETAILED DESCRIPTION OF THE INVENTION

Figure 1:
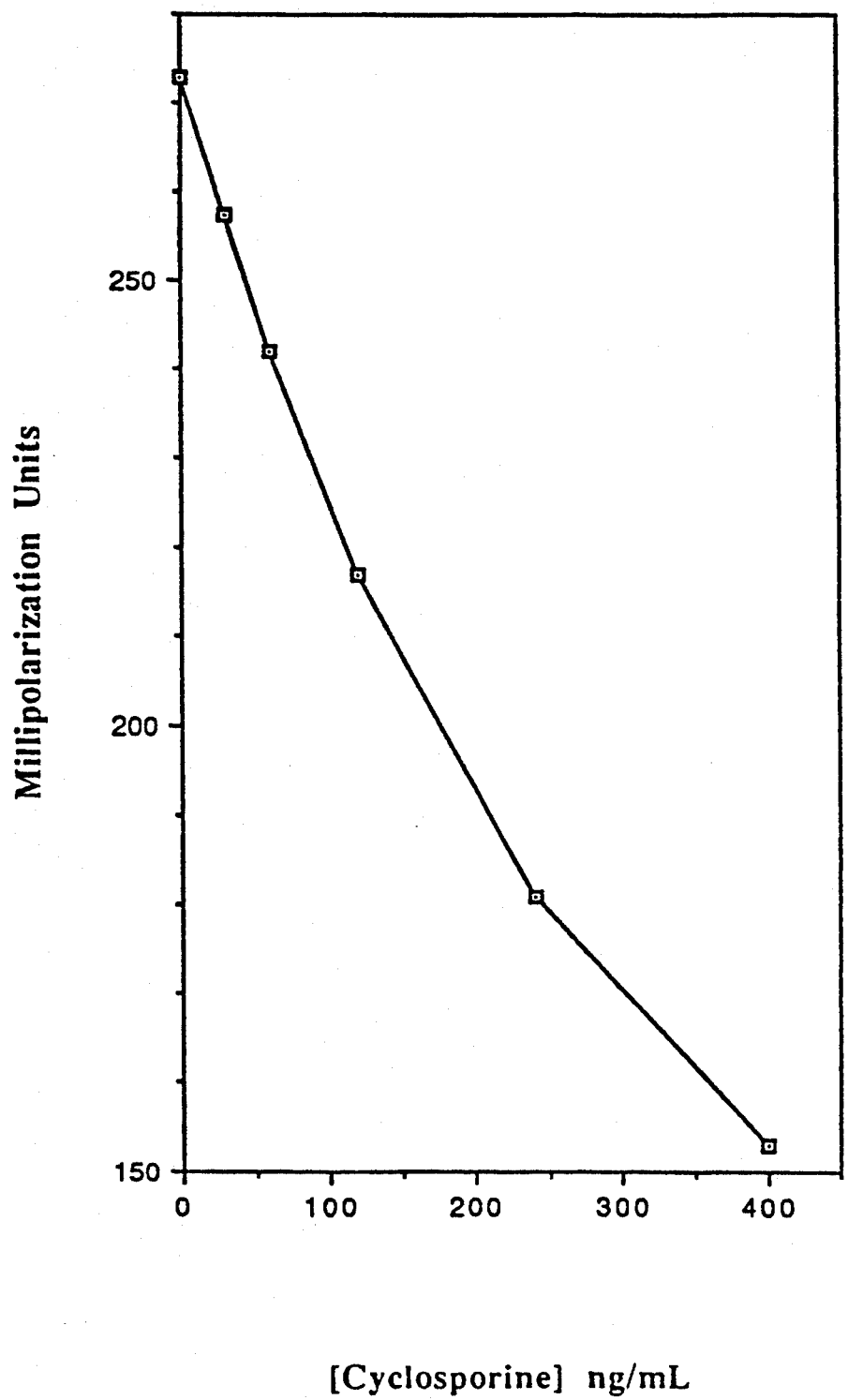
FIG. 1 illustrates a calibration curve employed to determine the amount cyclosporine from a serum sample in a fluorescent polarization immunoassay employing the precipitation reagent of the present invention.

The precipitation reagent of the present invention enables the extraction of hydrophobic analytes from a biological test sample, such as serum, plasma, whole blood, urine, spinal fluid, and the like. In particular, precipitation of interfering proteins, hemoglobin, and other interfering substances, are precipitated from the test sample to thereby render such analytes readily available for measurement by a desired analytical system. Although the precipitation reagent is particularly useful in analytical systems for determining hydrophobic analytes employing specific binding proteins, especially immunoassay systems, the precipitation reagent can be employed in other assay systems as well, such as radioassays and the like.

According to the present invention, the zinc salt component of the precipitation reagent is selected from the group consisting of zinc sulfate, zinc choride, zinc acetate, and the like. The zinc salt component participates in the precipitation of interfering proteins present in a test sample, such as serum albumin, lipoproteins, immunoglobulins, conjugated proteins such as bilirubin, and the like, as well as any hemoglobin which may be present in a test sample, such as in a whole blood test sample. The alcohol component of the precipitation reagent is selected from the group consisting of methanol, ethanol, propanol, butanol, and mixtures therof. The alcohol component participates in maintaining the hydrophobic analyte in solution, and precipitates proteins and conjugated proteins as well.

The glycol component of the precipitation reagent is selected from the group consisting of ethylene glycol, propylene glycol, polyethylene glycol, polypropylene glycol, glycerol and the like. The glycol component serves to decrease the toxicity of the other components of the precipitation reagent, particularly the alcohol component, and stabilizes cellular receptors and specific binding proteins which are employed in an assay system, particularly antibodies, by preserving the binding integrity thereof.

The acid component is selected from the group consisting of 5-sulfosalicylic acid, trichloroacetic acid, hydrochloric acid, acetic acid and the like, and serves to precipitate and denature interfering proteins.

A preferred precipitation reagent of the present invention for treating a serum test sample comprises a solution of zinc sulfate (10 mM), 70% (w/v) methanol, 25% (w/v) ethylene glycol, and 0.5 grams of 5-sulfosalicylic acid. Where the test sample is a whole blood test sample, the precipitation reagent preferably comprises a solution of zinc sulfate (60 mM), 50% (w/v) methanol, and 33% (w/v) ethylene glycol.

It is to be understood that hydrophobic analytes as contemplated by the present invention include, but are not intended to be limited to, steroids, cholesterol, drugs such as cyclosporine, and analogs thereof, and the like. Such hydrophobic analytes have a particularly high binding affinity for proteins, especially lipoproteins. Accordingly, in order to extract such hydrophobic analytes from such proteins which would otherwise interfere with the determination thereof as provided herein, the precipitation reagent is employed to accomplish such extraction wherein proteins present in the test sample are precipitated while, at the same time, recovering from between about 90% and 110% of the extracted analyte. In addition, the precipitation reagent according to the present invention will precipitate hemoglobin, serum albumin, serum immunoglobulins, lipoproteins, conjugated proteins, and the like.

When employing the precipitation reagent of the present invention for performing an immunoassay, the test sample is first treated with the precipitation reagent wherein the hydrophobic analyte is extracted and the interfering proteins are precipitated from the test sample. Although the interfering proteins may settle by gravity, such extraction of the analyte is preferably accomplished by centrifuging the treated test sample wherein the resulting supernatant contains the desired analyte, substantially free of such interfering proteins. The supernatant is then combined with a detectable tracer compound as would be known by one skilled in the art, and an appropriate antibody to, or binding agent for, the analyte, prepared according to methods known in the art. According to such general immunoassay procedure, the analyte present in the test sample and the tracer compound compete for a limited number of binding sites, resulting in the formation of analyte and tracer compound complexes. By maintaining a constant concentration of the tracer compound and the antibody, the ratio of the formation of analyte complex to tracer complex is directly proportional to the amount of analyte present in the test sample.

The precipitation reagent of the present invention is particularly useful in fluorescence polarization immunoassay systems wherein the amount of analyte in a test sample is determined by exciting an assay mixture with polarized light and measuring the polarization of the fluorescence emitted by any of the free or unbound tracer compound and tracer-antibody complex. Any of the tracer compound which is not complexed to an antibody is free to rotate in less than the time required for adsorption and re-emission of fluorescent light. As a result, the re-emitted light is relatively randomly oriented so that the fluorescence polarization of any of the tracer compound not complexed to the antibody is low, approaching zero. Upon complexing with a specific antibody, the tracer-antibody complex thus formed assumes the rotation of the antibody molecule, which is slower than that of the relatively small tracer compound molecule, thereby increasing the polarization observed. When making such determination, the analyte competes with the tracer compound for antibody sites wherein the observed polarization of fluorescence of the tracer-antibody complex becomes a value between the value of the free tracer compound and the value tracer-antibody complex. Accordingly, if the test sample contains a high concentration of analyte, the observed polarization value is closer to that of the free tracer compound, i.e., low. Conversely, if the test sample contains a low concentration of analyte, the polarization value is closer to that of the tracer-antibody complex, i.e., high. By sequentially exciting the reaction mixture of an immunoassay with vertically and then horizontally polarized light, and analyzing only the vertical component of the emitted light, the polarization of the fluorescence in the reaction mixture can be accurately determined. The precise relationship between polarization and concentration of the analyte is established by measuring the polarization values of calibrators having known concentrations, and the concentration of the analyte can be interpolated from a standard curve prepared therefrom.

When employing fluorescence polarization techniques, the results can be quantified in terms of "millipolarization units", "span" (in millipolarization units) and "relative intensity". The measurement of millipolarization units indicates the maximum polarization when a maximum amount of the tracer compound is bound to the antibody in the absence of any phenylclorobenzene (PCB) in the test sample. The higher the net millipolarization units, the better the binding of the tracer compound to the antibody. For the purposes of the present invention, a net millipolarization value of at least about 130 is preferred.

The "span" is an indication of the difference between the net millipolarization and the minimum amount of the tracer compound bound to the antibody. A larger span provides for a better numerical analysis of the data. For the purposes of the present invention, a span of at least about 15 millipolarization units is preferred.

The "relative intensity" is a measure of the strength of the fluorescence signal above the backgound fluorescence. Thus, a higher intensity will give a more accurate measurement. The intensity is determined as the sum of the vertically polarized intensity plus twice the horizontally polarized intensity. The intensity can range from a signal of about three times to about thirty times the backgound noise, depending upon the concentration of the tracer compound and other assay variables. For the purpose of the present invention, an intensity of about three to about twenty times that of background noise is preferred.

The precipitation reagent according to the present invention is particularly useful for performing a fluorescent polarization immunoassay for cyclosporine and metabolites thereof employing a fluorescent tracer compound comprising 4-aminomethylfluorescein coupled to the hydroxyl group of MeBmt (N-Methyl-(4R)-4-but-2E-en-1-yl-4-methyl-(L)-threonine at the first position of cyclosporine, as described by the copending U.S. patent application Ser. No. 07/567,840 filed Aug. 15, 1990, entitled "Immunoassay Reagents And Method For Determining Cyclosporine", and incorporated by reference herein, and a monoclonal antibody to cyclosporine, such as described by International Patent Application Publication No. WO 86/02080. According to such method, a solubilization reagent comprising saponin and a detergent such as Tergitol min foam IX TM [alkyoxy(polyethyleneoxypropyleneoxy)-isopropanol], such as described by the copending U.S. patent application Ser. No. 07/567,840 filed Aug. 15, 1990, entitled "Solubilization Reagent For Biological Test Samples", and incorporated by reference herein, a dilution buffer, and calibrators and controls are also employed. Such solubilization reagent is employed with, for example, a whole blood test sample or other biological test samples containing various cellular components, wherein it is desirable to dissociate any hydrophobic analytes from such cellular components in order to render such analytes available for binding to, for example, a specific binding protein such as an antibody.

Once the interfering proteins have been precipitated and the cyclosporine and metabolites thereof extracted as described above and, in the case of, for example, a whole blood test sample, the sample is first treated with the solubilization reagent as described above, the supernatant containing cyclosporine, or cyclosporine and metabolites of cyclosporine, is then combined with the antibody. Prior to addition of the tracer compound and dilution buffer, a background fluorescence reading is taken, wherein after an incubation period of from between about ten minutes and about thirty minutes, a fluorescence polarization reading is taken as described above.

The present invention will now be illustrated, but is not intended to be limited, by the following example:

FLUORESCENT POLARIZATION IMMUNOASSAY FOR CYCLOSPORINE

Reagents

The reagents for performing a fluorescence polarization immunoassay employing the precipitation reagent according to the present invention were prepared as follows:

(a) Cyclosporine Tracer Reagent (i) Preparation of [O-(Chloroformyl)MeBmt[1] cyclosporine (Cyclosporine chloroformate)

Cyclosporine (24.2 mg, 0.020 mmoles) was dissolved in a 25%w/w solution of phosgene in benzene (2.0 mL) in a 10mL round bottom flask fitted with stopper and stirbar. The reaction was stirred for 5 minutes to dissolve the cyclosporine, then was allowed to stand undisturbed at room temperature for 24 hours. The reaction was concentrated in vacuo, and the product could be stored as a solid at 0° C. for up to six months. For subsequent reactions, a 0.02M solution in DMF was used.

(ii) Preparation of [O-(Fluorescein-4'-ylmethylaminoformyl)-MeBmt][1] cyclosporine Cyclosporine chloroformate (0.2 mL, 4 moles), as a 0.02M solution in DMF as described in step (i) above was combined with 4'-aminomethylfluorescein hydrochloride (2.0 mg, 5 moles) in a stoppered vial fitted with a stirbar. Pyridine was added until the apparent pH (by moist pH paper) was approximately 7. The reaction was stirred at room temperature for 24 hours. The solvent was removed in vacuo, and the residue was taken up in methanol and loaded onto a 1 mm silica gel plate. The plate was developed with 15% methanol/methylene chloride. The product band, Rf 0.55, was eluted from the silica gel with methanol.

(iii) Preparation of Tracer Reagent

A 60 nanomolar cyclosporine tracer reagent was prepared comprising the cyclosporine tracer compound prepared according to step (ii) above in 0.1 M sodium phosphate buffer, pH 7.5, containing 0.01 % (w/v) bovine gamma globulin, 0.1 % (w/v) sodium azide, 5.0% (w/v) ethylene glycol and 0.05% (w/v) Tween TM 20.

(b) Monoclonal Antibody Formulation

A monoclonal antibody reagent was prepared comprising mouse (ascites) monoclonal antibody to cyclosporine (Sandoz AG, Basle, Switzerland) diluted with citrate buffer including sodium azide.

(c) Pretreatment Reagent

A pretreatment reagent was prepared comprising 0.1 M Tris TM buffer, pH 7.5, 0.1% (w/v) sodium azide, 0.5% (w/v) copper sulfate and 10.0% (w/v) 5-sulfosalicylate.

(d) Dilution Buffer

A dilution buffer was prepared comprising 0.1 M sodium phosphate, pH 7.5, and 0.1 % (w/v) bovine gamma globulin.

(e) Serum Precipitation Reagent

A serum precipitation reagent was prepared comrising 10 mM zinc sulfate in an aqueous diluent with 70% (w/v) ethylene glycol, 25% (w/v) methanol, and 0.5 grams 5-sulfosalicylic acid.

(f) Whole Blood Precipitation Reagent

A whole blood precipitation reagent was prepared comprising 60 mM zinc sulfate, 50% (w/v) methanol and 30% ethylene glycol.

(g) Solubilization Reagent

A solubilization reagent was prepared comprising 2.0% (w/v) Tergitol min foam TM, 2.0% (w/v) saponin and 0. 1% (w/v) sodium azide.

(h) Calibrators

Cyclosporine monoclonal whole blood calibrators were prepared comprising cyclosporine and an artificial human whole blood matrix. The calibrators were prepared at concentrations of 0.0, 100, 250, 500, 1000, and 1500 nanograms per milliliter, with sodium azide as a preservative.

(i) Controls

Cyclosporine monoclonal whole blood controls were prepared comprising cyclosporine and an artificial human whole blood matrix. The controls were prepared at concentrations of 150, 400 and 800 nanograms per milliliter, with sodium azide as a preservative.

Cyclosporine Serum FPIA Assay Protocol

A fluorescent polarization immunoassay for determining cyclosporine in a serum sample employing an Abbott TDx ® Therapeutic Drug Monitoring Analyzer was performed as follows:

Fifty microliters each of patient serum samples containing cyclosporine, controls and calibrators were pipetted into labeled centrifuge tubes. A pipette was filled with the serum precipitation reagent, purged of air bubbles, and 150 microliters were dispensed into each centrifuge tube by touching the end of the pipette tip to the wall of each centrifuge tube while dispensing the reagent. The centrifuge tubes were then capped and mixed on a vortex mixer for ten seconds and placed into a centrifuge head so that the tubes were evenly distributed so that the centrifuge head was balanced. The tubes were centrifuged for approximately three minutes at 9,500× g until a clear supernatant and a hard, compact pellet of denatured protein was obtained. After centrifugation was complete, each tube was uncapped and the supernatant was decanted into the corresponding sample well of a TDx Sample Cartridge.

The fluorescence polarization value of each calibrator, control and sample was determined and printed on the output tape of the Abbott TDx Analyzer. A standard curve was generated in the instrument by plotting the polarization, P, of each calibrator versus its concentration using a nonlinear regression analysis wherein, the concentration of each control and sample was read off the stored calibration curve (FIG. 1) and printed on the output tape.

The sensitivity of the preferred fluorescence polarization assay according to the present invention is 15.0 nanograms/milliliter of cyclosporine and metabolites. When compared to an available radioimmunoassay using 60 clinical samples, a linear least squared regression analysis gave a slope of 0.947, an intercept of 7.15, and a correlation coefficient of 0.969.

Where a test kit according to the present invention is being used in conjunction with the TDx Analyzer, the reagents for performing the fluorescent polarization immunoassay according to the present invention can be contained in separate vials of a TDx Reagent Pack wherein vial caps from each of the vials in the Reagent Pack are removed and placed into designated wells inside the Reagent Pack. Accordingly, once the Reagent Pack is placed inside the TDx Analyzer, the assay procedure heretofore is fully automated.

If a manual assay is being performed, the test sample is first treated with the precipitation reagent as described above, and then mixed with the dilution buffer. The antibody reagent and the pretreatment solution are then placed into the test tube containing the sample, and a backgound fluorescence reading is taken. The tracer compound and dilution buffer are added to the sample, and after incubation, a fluorescence polarization reading is taken.

CYCLOSPORINE WHOLE BLOOD FPIA ASSAY PROTOCOL

Figure 2:
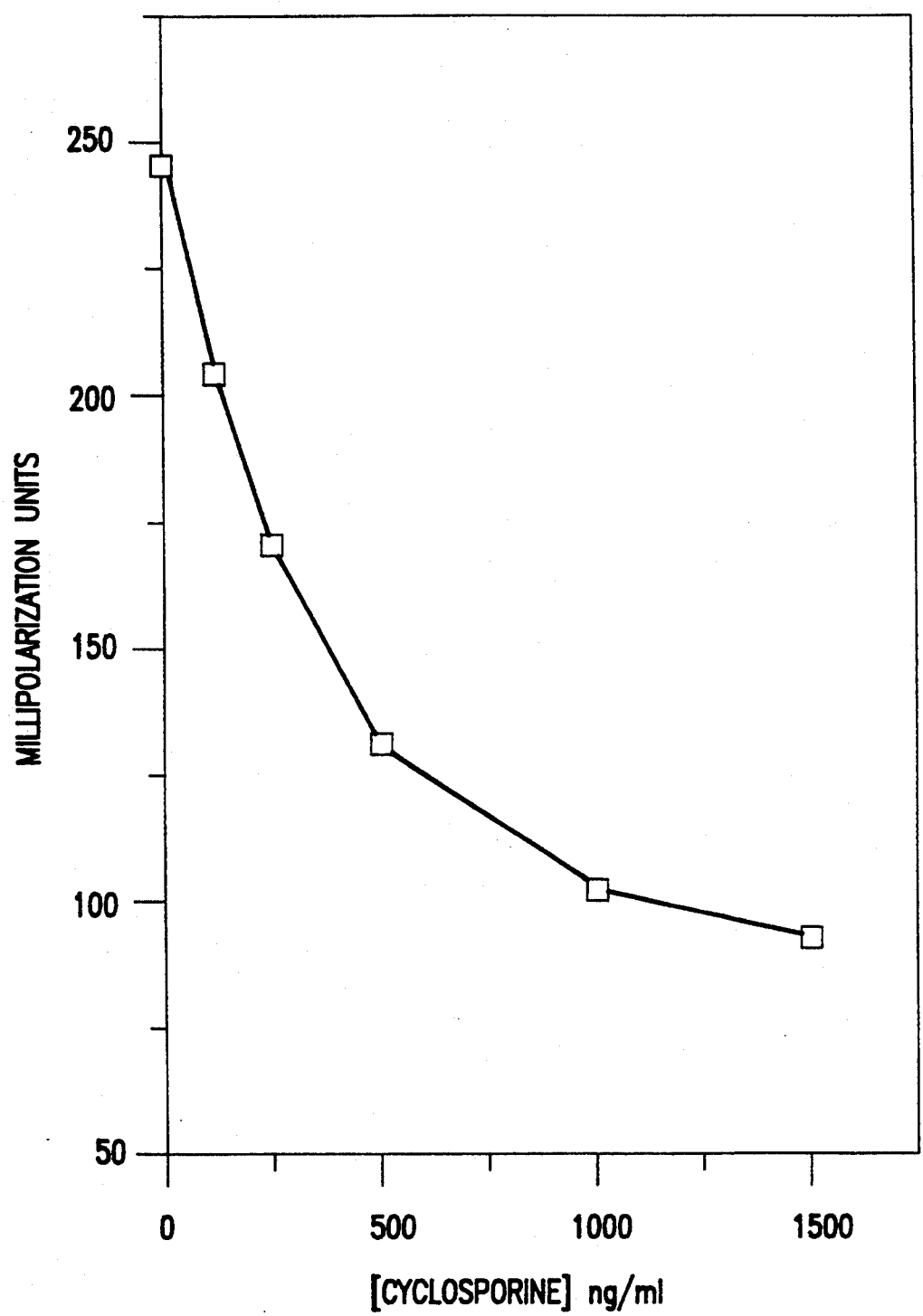
FIG. 2 illustrates a calibration curve employed to determine the amount cyclosporine from a whole blood sample in a fluorescent polarization immunoassay employing the precipitation reagent of the present invention.

A fluorescent polarization immunoassay for determining cyclosporine in a whole blood test sample employing an Abbott TDx ® Therapeutic Drug Monitoring Analyzer was performed as follows:

One hundred-fifty microliters each of patient whole blood samples containing cyclosporine, controls and calibrators were pipetted into labeled centrifuge tubes, and 50 microliters of the solubilization reagent were added to each of the tubes. A pipette was filled with the whole blood precipitation reagent, purged of air bubbles, and 300 microliters were dispensed into each centrifuge tube by touching the end of the pipette tip to the wall of each centrifuge tube while dispensing the reagent. The centrifuge tubes were then capped and mixed on a vortex mixer for ten seconds and placed into a centrifuge head so that the tubes were evenly distributed so that the centrifuge head was balanced. The tubes were centrifuged for approximately five minutes at 9,500× g until a clear supernatant and a hard, compact pellet of denatured protein was obtained. After centrifugation was complete, each tube was uncapped and the supernatant was decanted into the corresponding sample well of a TDx Sample Cartridge and the fluorescence polarization value of each calibrator, control and sample was determined and printed on the output tape of the Abbott TDx Analyzer as described above. A standard curve was generated in the instrument by plotting the polarization, P, of each calibrator versus its concentration using a nonlinear regression analysis wherein, the concentration of each control and sample was read off the stored calibration curve (FIG. 2) and printed on the output tape.

It will be apparent that many modifications and variations of the present invention as herein set forth are possible without departing from the spirit and scope hereof, and that, accordingly, such limitations are imposed only as indicated by the appended claims.

We claim:

1. An immunoassay test kit comprising in separate containers a reagent useful for precipitating proteins and extracting a hydrophobic analyte from a biological test sample and a specific binding agent for said analyte, said reagent comprising from about 5.0 mM to about 100.00 mM of a zinc salt, from about 5 percent (weight/volume) to about 50 percent (weight/volume) of a glycol, a glycerol or a combination thereof, and from about 30 percent (weight/volume) to about 100 percent (weight/volume) of a straight or branched chain alcohol having from 1 to 4 carbon atoms.

2. The immunoassay test kit of claim 1 wherein said zinc salt is selected from the group consisting of zinc sulfate, zinc chloride and zinc acetate.

3. The immunoassay test kit of claim 1 wherein said zinc salt is zinc sulfate.

4. The immunoassay test kit of claim 1 wherein said glycol is selected from the group consisting of ethylene glycol, propylene glycol, polyethylene glycol, and polypropylene glycol.

5. The immunoassay test kit of claim 1 wherein said glycol is ethylene glycol.

6. The immunoassay test kit of claim 1 wherein said alcohol is selected from the group consisting of methanol, ethanol, propanol, butanol, and mixtures thereof.

7. The immunoassay test kit of claim 1 wherein said alcohol is methanol.

8. The immunoassay test kit of claim 1 further comprising from about 0 percent (weight/volume) to about 20 percent (weight/volume) of an acid selected from the group consisting of 5-sulfosalicylic acid, trichloroacetic acid, hydrochloric acid and acetic acid.

9. The immunoassay test kit of claim 8 wherein said acid is 5-sulfosalicylic acid.

10. The immunoassay test kit of claim 1 wherein said test sample is selected from the group consisting of serum, plasma and whole blood.

11. In an immunoassay method for determining a hydrophobic analyte in a biological test sample which assay includes utilizing a precipitation reagent to remove interfering proteins from said sample prior to immunological detection of said analyte wherein the improvement comprises utilizing as the precipitation reagent, a precipitation reagent comprising from about 5.0 mM to about 100.00 mM of a zinc salt, from about 5 percent (weight/volume) to about 50 percent (weight/volume) of a glycol, a glycerol or a combination thereof, and from about 30 percent (weight/volume) to about 100 percent (weight/volume) of a straight or branched chain alcohol having from 1 to 4 carbon atoms.

12. The method of claim 11 wherein said zinc salt is selected from the group consisting of zinc sulfate, zinc chloride and zinc acetate.

13. The method of claim 11 wherein said zinc salt is zinc sulfate.

14. The method of claim 11 wherein said glycol is selected from the group consisting of ethylene glycol, propylene glycol, polyethylene glycol, and polypropylene glycol.

15. The method of claim 11 wherein said glycol is ethylene glycol.

16. The method of claim 11 wherein said alcohol is selected from the group consisting of methanol, ethanol, propanol, butanol, and mixtures thereof.

17. The method of claim 11 wherein said alcohol is methanol.

18. The method of claim 11 wherein said precipitation reagent further comprises an acid selected from the group consisting of 5-sulfosalicylic acid, trichloroacetic acid, hydrochloric acid and acetic acid.

19. The method of claim 18 wherein said acid is 5-sulfosalicylic acid.

20. The method of claim 11 wherein said test sample is selected from the group consisting of serum, plasma and whole blood.

* * * * *